United States Patent
Carmichael et al.

(10) Patent No.: US 6,265,167 B1
(45) Date of Patent: *Jul. 24, 2001

(54) TARGETED RNA DEGRADATION USING NUCLEAR RIBOZYME RNA

(76) Inventors: Gordon G. Carmichael, 103 Richmond La., West Hardford, CT (US) 06117; David B. Batt, 2090 Stanley St., Apt. 102, New Britain, CT (US) 06053; Zhong Liu, 173 Edwards St., New Haven, CT (US) 06511

( * ) Notice: Subject to any disclaimer, the term of this patent is extended or adjusted under 35 U.S.C. 154(b) by 0 days.

This patent is subject to a terminal disclaimer.

(21) Appl. No.: 09/314,083

(22) Filed: May 18, 1999

Related U.S. Application Data

(63) Continuation of application No. 08/160,058, filed on Dec. 1, 1993, now Pat. No. 5,908,779.

(51) Int. Cl.[7] .............................. C12Q 1/68; C12N 15/63; C12N 15/85; C07H 21/04
(52) U.S. Cl. .................... 435/6; 435/91.1; 435/320.1; 435/325; 536/23.1; 536/24.5
(58) Field of Search ................................ 435/6, 91.1, 325, 435/320.1; 536/23.1, 24.5

(56) References Cited

U.S. PATENT DOCUMENTS 5,908,779 * 6/1999 Carmichael et al. ................ 435/325

* cited by examiner

*Primary Examiner*—Andrew Wang
(74) *Attorney, Agent, or Firm*—Steven J. Moore; Cummings & Lockwood

(57) ABSTRACT

The invention pertains to a novel method and construct for regulating gene expression through inhibition of gene expression by nuclear antisense RNA. The construct provides an efficient means for introducing, expressing and accumulating the antisense RNA in the nucleus. The antisense RNA hybridizes to the sense mRNA in the nucleus, thereby preventing both processing and cytoplasmic transport. The construct comprises a promoter, antisense sequences, and a cis- or trans-ribozyme which generates 3'-ends independently of the polyadenylation machinery and thereby inhibits the transport of the RNA molecule to the cytoplasm. The construct may also comprise a histone stem-loop structure that assists in stabilizing the transcripts against exonucleolytic degradation.

20 Claims, 5 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:1:

```
GGAUCCCCCG AAUUAAUUCG GCCCUUAUCA GGGCCAUGCU AGUCGCGGCC GCCUCCGCGG        60

CCGCCUGAUG AGUCCGUGAG GACGAAACAU GCAUAUCAAG CUU                         103
```

TARGETED RNA DEGRADATION USING NUCLEAR RIBOZYME RNA

RELATED APPLICATIONS

This application is a Continuation of U.S. application Ser. No. 08/160,058, filed Dec. 1, 1993, now U.S. Pat. No. 5,908,779, the contents of which are incorporated herein by reference in their entirety.

GOVERNMENT SUPPORT

This work was supported by grant CA45382 from the National Cancer Institute. The Government has certain rights in the invention.

BACKGROUND OF THE INVENTION

The polyoma virus genome is a small circular double-stranded DNA molecule whose early and late transcription units proceed in opposite directions from an intergenic regulatory region. In the early phase of a productive life cycle, the early genes (encoding the large, middle and small T antigens) are preferentially expressed. Before the initiation of viral DNA replication, few late-strand messages can be detected (Beard et al., *J. Virol.* 17:20–26 (1976)). Once the infection enters the late phase (after the onset of DNA replication), late gene expression increases rapidly while the relative level of early gene expression is dramatically reduced.

The observation that polyoma virus mutants with temperature sensitive large T antigens overexpress their early genes at the nonpermissive temperature has led to the proposal that the viral early genes are negatively regulated by their own products (Farmerie and Folk, *Proc. Natl. Acad. Sci. USA* 81:6919–6923 (1984)). This autoregulation was thought to result from large T antigen binding to high affinity binding sites in the viral intergenic region and thereby inhibiting initiation from the early promoter (Fenton and Basilico, *Virology* 121:384–392 (1982)). However, it has been shown using nuclear run-on assays that the relative transcriptional activities from the early and late promoters change little throughout infection (Hyde-DeRuyscher and Carmichael, *Proc. Natl. Acad. Sci. USA* 85:8993–8997 (1988)). Regulation of early gene expression after transcription initiation is also consistent with the data of Farmerie and Folk (Ibid.), who observed early gene repression by large T antigen even in constructs where this transcription was driven by a heterologous promoter. Taken together these results suggest that regulation of early gene expression is at a post-transcriptional level.

It has been shown that transcription termination of the late genes is inefficient during the late phase of infection (Hyde-DeRuyscher and Carmichael, Ibid.), allowing RNA polymerase II to continue around the circular viral genome multiple times. The resulting giant primary transcripts are eventually processed by RNA splicing and polyadenylation, but unprocessed giant transcripts accumulate to high levels in the nucleus (Acheson, *Mol. Cell. Biol.* 4:722–729 (1984)). Due to the circularity of the polyoma genome, giant late-strand transcripts contain sequences complementary to early-strand transcripts, serving as natural antisense RNA. These giant transcripts accumulate at the same time that early-strand RNAs become relatively less abundant.

There is a growing body of literature devoted to antisense technology; however, this work has related only to cytoplasmic antisense RNA. (Murray, J. A. H. and Crockett, N., "Antisense Techniques: An Overview, " in *Antisense RNA and DNA,* (Wiley-Liss, Inc.) pp. 1–49 (1992)). There has been no work to date aimed at producing antisense RNA accumulated in the nucleus.

SUMMARY OF THE INVENTION

This invention pertains to the regulation of gene expression by nuclear antisense RNA. It is shown herein that the naturally occurring polyoma antisense early RNA generated from the late transcription unit is almost exclusively present in the nucleus. Furthermore, it is shown herein that polyoma early-strand RNAs are reduced by expression and accumulation in the nucleus of antisense-early RNAs. It is demonstrated that antisense RNAs can be expressed and accumulated in the nucleus using a construct comprising a promoter, antisense sequences, and sequences encoding a cis-ribozyme and optionally a stem loop structure. The cis-ribozyme is incorporated into the antisense construct in order to generate 3'-ends independently of the polyadenylation machinery and thereby inhibit transport of the RNA molecule to the cytoplasm. The construct may optionally contain a histone stem loop structure to aid in stabilizing the transcripts against exonucleolytic degradation. This invention has application to several areas. It may be used as a therapeutic agent, targeting and inhibiting harmful native gene expression. It may also be used therapeutically to inhibit viral gene expression, thereby making cells resistant to and curing viral infection. This invention also has application as a research tool with the ability to inhibit expression of any targeted gene.

BRIEF DESCRIPTION OF THE DRAWINGS

FIG. 2A shows antisense constructs used in this study. Construct αE-RZ contains the antisense polyoma early region driven by the cytomegalovirus (CMV) promoter, with 3' end formation the result of cleavage by a cis-ribozyme. Construct E-RZ contains the same polyoma early region and the ribozyme sequence but no CMV promoter or polyoma replication origin. Construct Py-CMV contains only the CMV promoter and polyoma replication origin. The orientation of the polyoma early region is indicated by the arrowheads. The RNA probe Ribo-Ava is also shown.

FIG. 2B shows the sequence of the ribozyme and the histone stem-loop structure used in the construction of the plasmids shown in FIG. 2A. The vertical arrow indicates the cleavage site of the cis-ribozyme. The optional histone stem-loop structure used to stabilize the transcripts against possible exonucleolytic degradation is indicated.

FIG. 4A shows inhibition of early-strand RNAs by antisense RNA in trans. Lane 1: wild type transfection; lanes 2–5: the same amount of mutant 5'ssΔ was transfected by itself (lane 2), or co-transfected with a 9 fold molar excess of αE-RZ (lane 3), E-RZ (lane 4) and Py-CMV (lane 5), respectively.

FIG. 4B shows dose-dependent effect of antisense RNA on polyoma early transcripts. The same amount of 5'ssΔ was co-transfected with nuclear antisense RNA expression vector αE-RZ at various molar ratios as indicated. The relative levels of early-strand RNAs are shown. Values have been corrected for probe length and U content. The numbers shown represent the average of two independent sets of experiments.

DETAILED DESCRIPTION OF THE INVENTION

Figure 1:
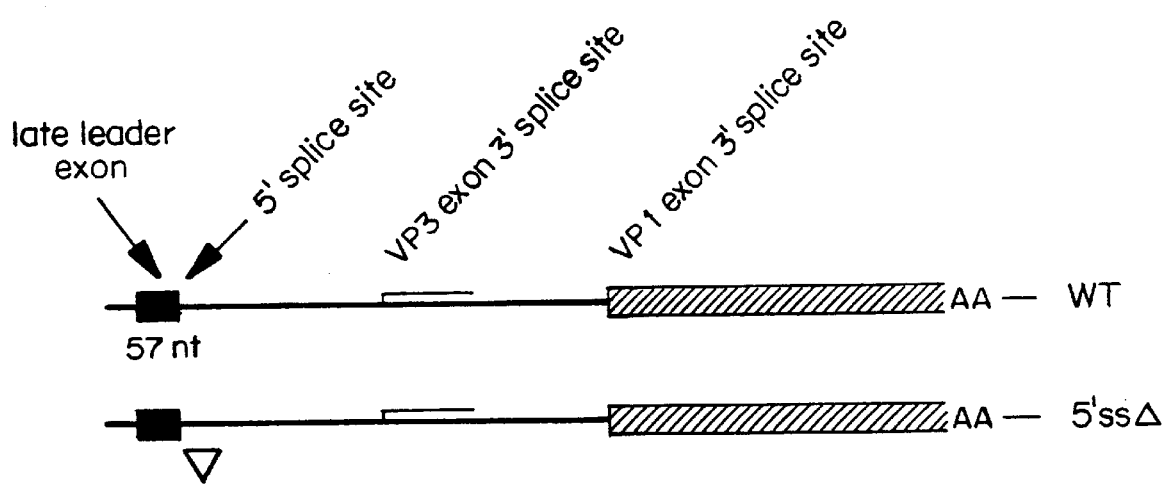
FIG. 1 depicts the "late" transcription units of the polyoma mutants used in this study. Wild type (WT) encodes the late leader exon and two alternative splice sites, used for production of messages for the structural proteins VP3 and VP1. Mutant 5'ssΔ lacks 6 nucleotides (nt) (GTAAGT) at the 5' splice site bordering the late leader exon and expresses lower than wild type levels of antisense RNA to the viral early region (Barrett et al., *Nucleic Acids Res.* 19:3011–3017 (1991).

The present invention pertains to a novel method and construct for regulating gene expression through inhibition of gene expression by nuclear antisense RNA. The construct provides an efficient means for introducing, expressing and accumulating the antisense RNA in the nucleus. The antisense RNA hybridizes to the sense mRNA in the nucleus, thereby preventing both processing and cytoplasmic transport. The construct comprises a promoter, an origin of replication, antisense sequences, and a cis- or trans-ribozyme which generates 3'-ends independently of the polyadenylation machinery and thereby inhibits the transport of the RNA molecule to the cytoplasm. The construct may also comprise a histone stem-loop structure that assists in stabilizing the transcripts against exonucleolytic degradation.

The advantages of this invention over prior cytoplasmic antisense technology are three-fold. First, this invention closely mimics the system of naturally-occurring antisense regulation seen in a variety of organisms, indicating that it is a natural means for studying antisense regulation of gene expression. Also, this invention solves at least one problem created by cytoplasmic antisense RNA, namely the activation of interferon by double stranded RNAs. There is no indication that nuclear antisense RNA causes interferon activation, and therefore there is less risk of adverse effects on the cell. (Lengyel, P., *Journal of Interferon Research* 7:511–519 (1987)). Furthermore, the efficiency of nuclear antisense RNA far exceeds that of cytoplasmic RNA. While in cytoplasmic RNA experiments the ratio of antisense to sense transcripts required for inhibition is typically on the level of 100 or 1000 to 1, data from nuclear antisense experiments indicates that the same level of regulation can be achieved with an antisense to sense ratio of as little as 5 to 1. This enhanced effectiveness is of great advantage both from an efficiency and cost-effectiveness standpoint.

Once introduced into the cell nucleus, the construct begins expressing the antisense sequences following the promoter. The construct contains none of the usual transcription termination sequences (typically associated with polyadenylation signals); instead a cis- or trans-ribozyme (SEQ ID NO. 1) is inserted to cleave the transcript without normal polyadenylation. This variation prohibits transportation of the antisense sequences from the nucleus to the cytoplasm. As the antisense sequences accumulate in the nucleus, they hybridize to their complementary sense RNA transcripts. It is believed that the formation of these hybrids prevents processing and cytoplasmic transport of the RNA, as these hybrids are shown to remain in the nucleus and are eventually degraded. By hybridizing to a targeted gene, the antisense transcripts can regulate and inhibit expression of that gene. This function has utility in both therapeutic and research applications.

The promoter segment can be chosen from a wide range of constitutive or inducible promoters. Of particular interest but not exclusive are the constitutive promoters of the human cytomegalovirus (CMV) and Rous sarcoma virus (RSV), as well as the Simian virus 40 and Herpes simplex promoters. Useful inducible promoters include antibiotic resistant promoters, heat-shock promoters, the hormone-inducible mammary tumor promoter and the metallotheionein promoter.

The ribozyme component is included for the purpose of producing the 3' end independent of the cellular polyadenylation machinery. A cis-ribozyme with the ability to generate 3' ends in this manner is expected to achieve the desired result; however, of particular interest are the hammerhead cis-ribozyme (described in the Examples) and the human hepatitis delta virus ribozyme, which is believed to cleave transcripts faster and more efficiently than the hammerhead ribozyme. Trans-ribozymes can be used as an alternative.

This invention has application to the regulation of genes, and therefore the antisense sequences of interest are numerous. However, the sequence of the target gene should be known before its complementary antisense can be created. Thus, antisense sequences can be utilized based on the sequence of the gene desired for targeting.

The construct of this invention may optionally contain a histone stem-loop structure for the purpose of stabilizing the cleaved antisense transcript against exonucleolytic degradation. However, depending on the desired duration of the result, this component may be omitted. In fact, published evidence (Eckner et al.) suggests that this structure stabilizes RNAs only in the cytoplasm.

Figure 2A:
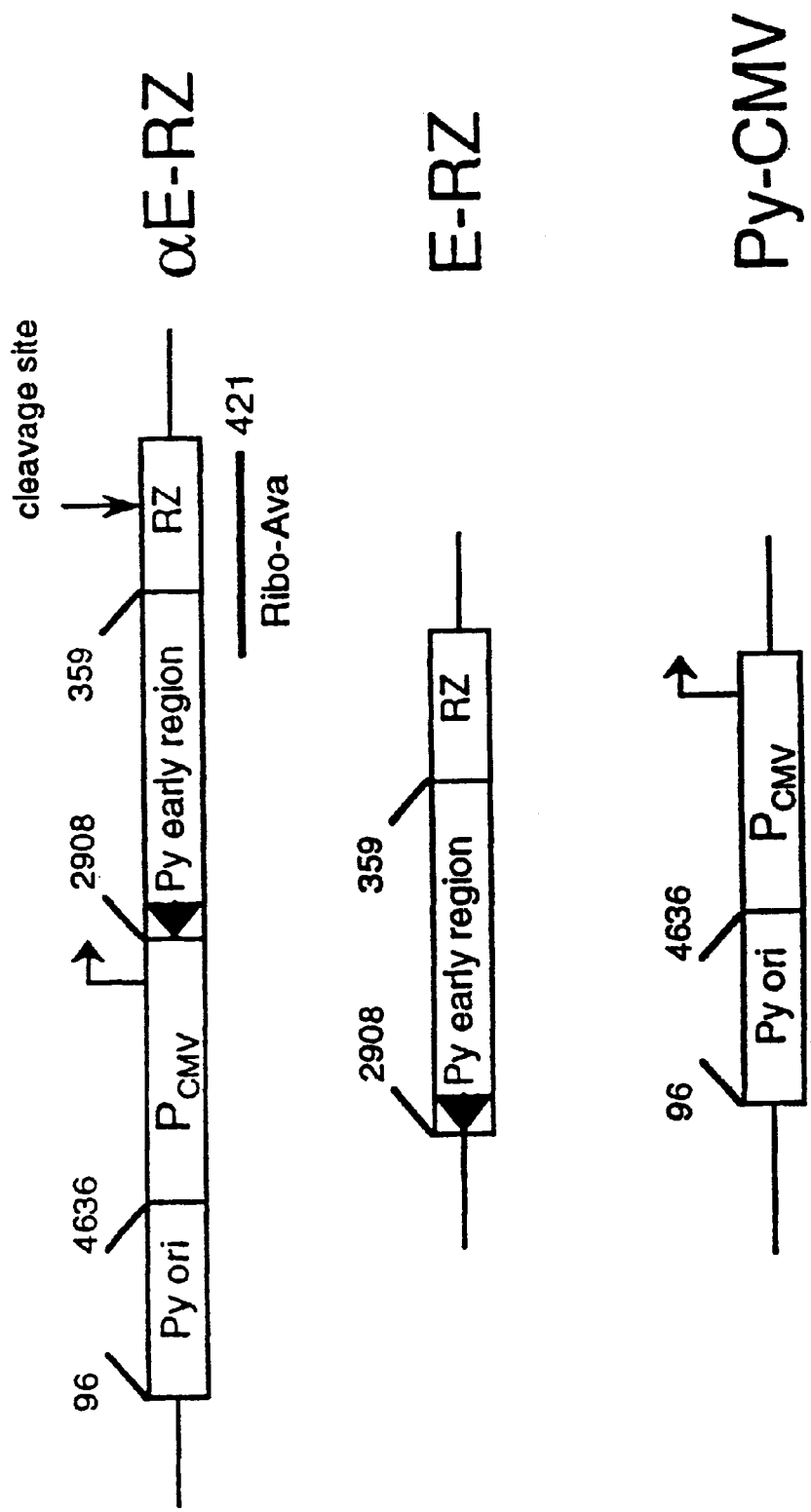
FIGS. 2A and 2B show constructs expressing antisense early RNA in the nucleus.
Figure 2B:
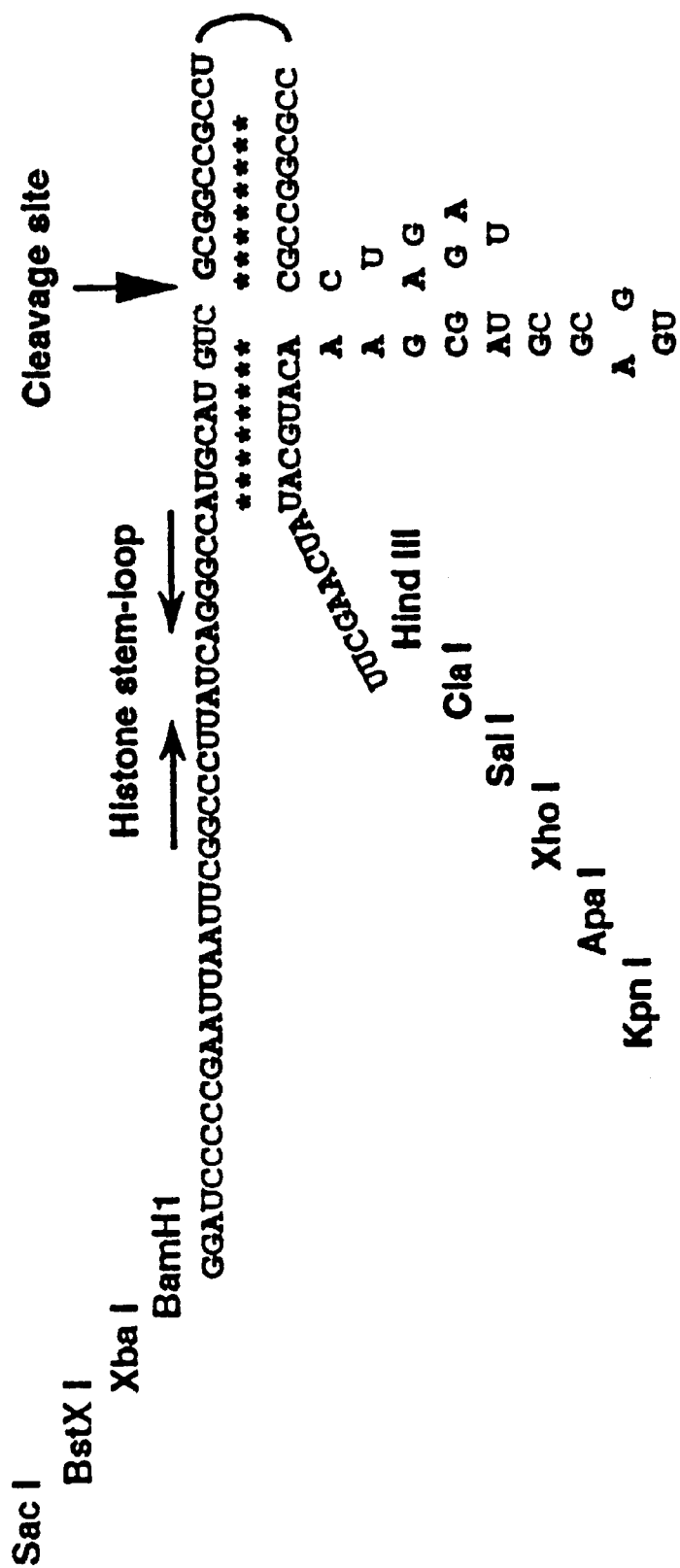

In a preferred embodiment, regulation of target gene expression is achieved using a novel DNA construct shown in FIG. 2A. This construct, αE-RZ, contains sequences encoding a self-cleaving ribozyme (FIG. 2B), flanked by a number of unique restriction enzyme cleavage sites, to facilitate cloning into other constructs. Immediately upstream of the ribozyme is a histone stem-loop structure to possibly retard degradation. The ribozyme cassette is inserted into standard cloning vector pBlueScript SKII. This ribozyme cassette is then excised and inserted into construct αE-RZ (FIG. 2A). This preferred embodiment incorporates a functional polyoma virus replication origin (nt 4636–96) to allow replication and amplification in mouse cells in the presence of large T antigen. Construct αE-RZ also contains a promoter derived from the human cytomegalovirus (CMV) downstream from the origin of replication. A number of unique restriction enzyme cleavage sites for insertion of antisense sequences are downstream of the promoter sequence. Located between the promoter and ribozyme cassette are the polyoma antisense-early sequences. These sequences include polyoma nt 359–2908, spanning from about 230 base pairs (bp) downstream of the early TATA consensus sequence to a nucleotide 5 bp upstream of the early polyadenylation signal, AAUAAA.

Figure 3:
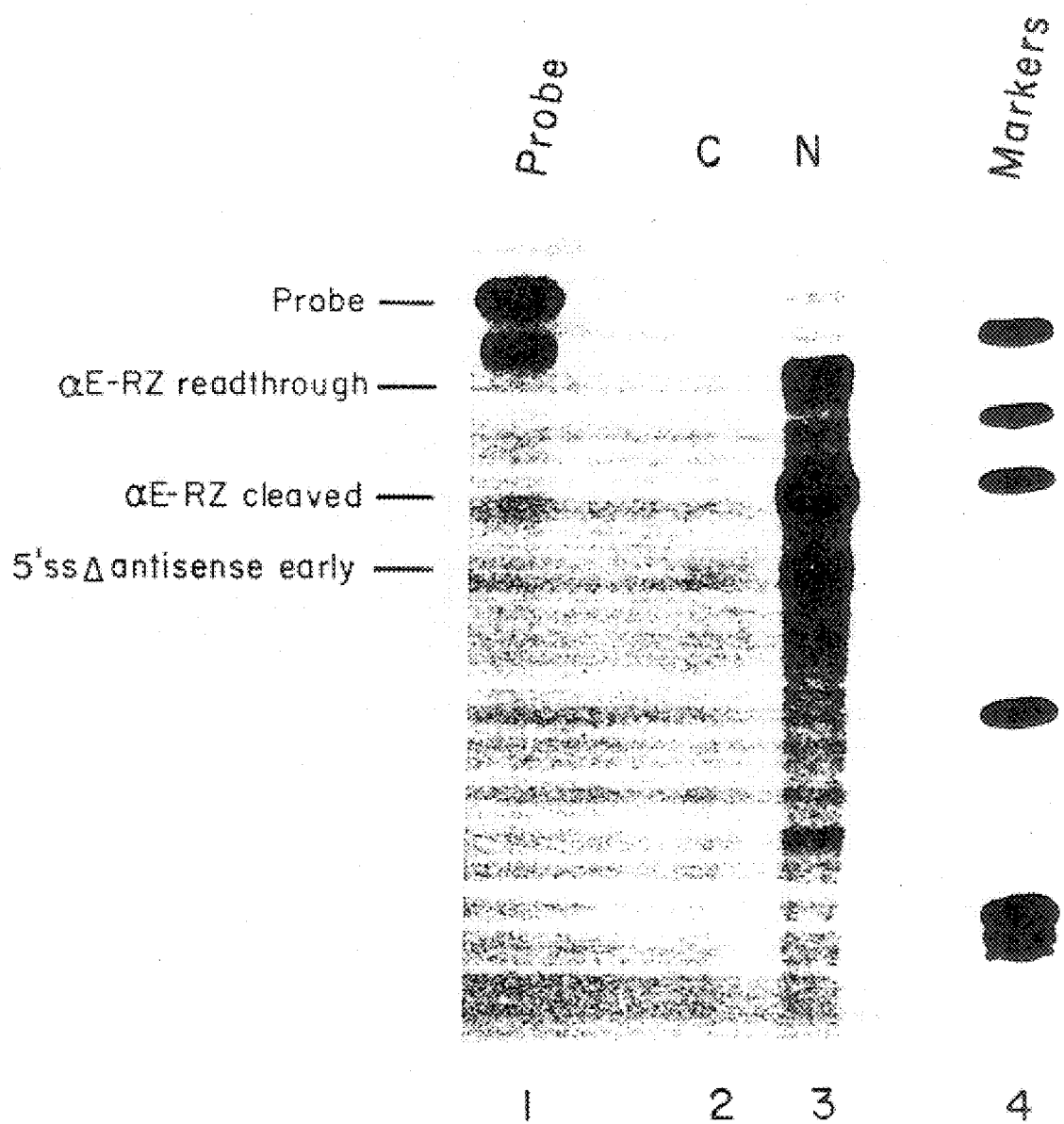
FIG. 3 illustrates subcellular distribution of antisense RNA transcripts produced by construct αE-RZ. This subcellular distribution was determined in cells cotransfected with construct αE-RZ (the antisense expression vector) and mutant 5'ssΔ (the target plasmid). Mutant 5'ssΔ was used because it overexpresses early RNA and allows αE-RZ replication. Virtually all antisense RNA produced from construct αE-RZ remains in the nucleus. It is also evident that ribozyme cleavage is incomplete, with only about 80% of the transcripts being cleaved. However, uncleaved transcripts also remain in the nucleus, as do the antisense-early transcripts from mutant 5'ssΔ.
Figure 4A:
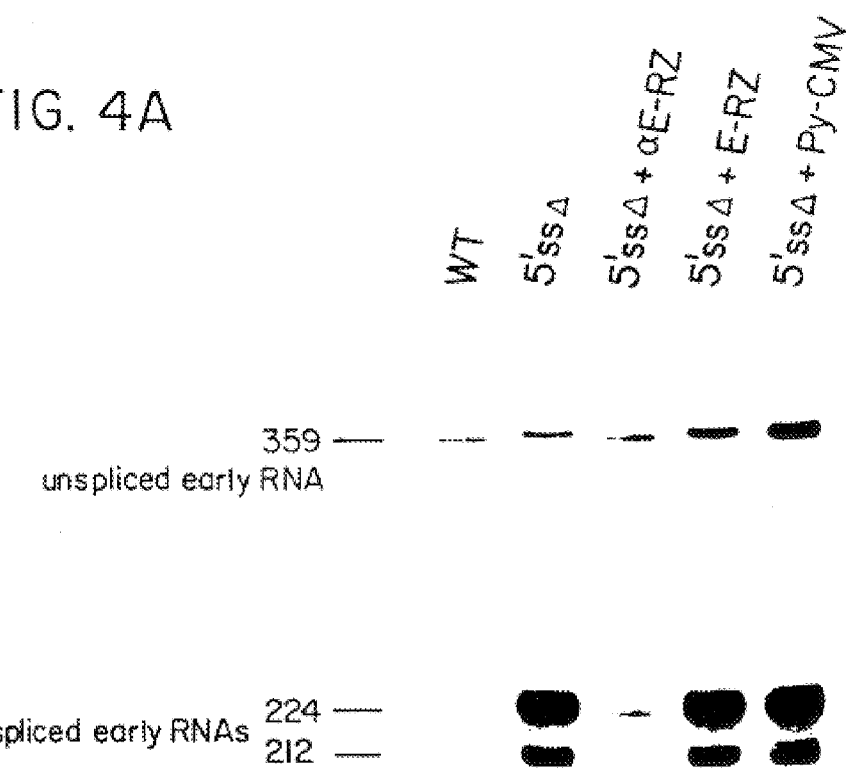
FIGS. 4A and 4B show dose-dependent inhibition of early-strand RNA accumulation by nuclear antisense RNA in trans.
Figure 4B:
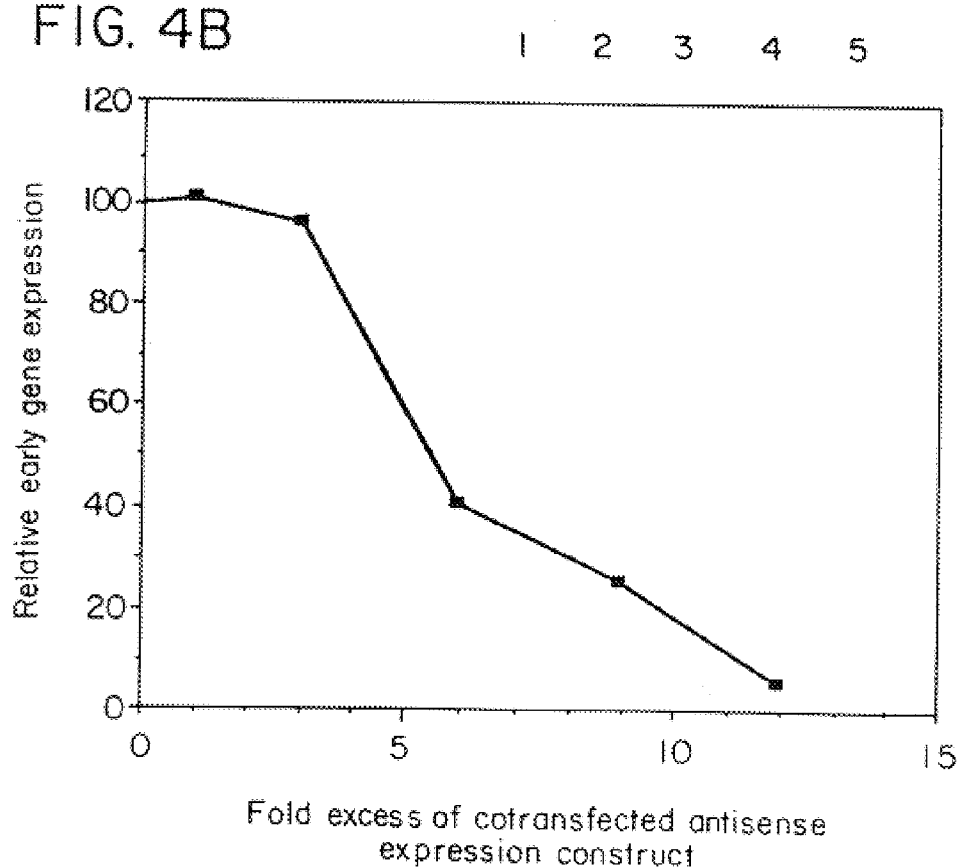

Mouse NIH 3T3 cells were co-transfected with construct αE-RZ and mutant 5'ssΔ. This polyoma virus mutant lacks 6 nt at the 5' splice site bordering the late leader, and overexpresses early-strand RNA by approximately 3 fold in comparison with wild type (FIG. 1). Thus, this mutant was used in place of wild type polyoma virus to allow more accurate determinations of antisense regulation. Nuclear and cytoplasmic RNA samples were isolated, and these samples were probed with an RNA probe that detects antisense early sequences from both constructs. The results (FIG. 3) showed that essentially all antisense RNA produced from construct αE-RZ remains in the nucleus, as does the RNA from the mutant 5'ssΔ. In further experiments a constant amount of construct 5'ssΔ was co-transfected into NIH 3T3 cells with increasing levels of αE-RZ, and early RNA levels from construct 5'ssΔ were measured using an RNAse protection assay as described in the Examples. These results (FIG. 4) confirm that while mutant 5'ssΔ over expresses nuclear early RNAs relative to wild type, when this construct is co-transfected with a nine-fold excess of construct αE-RZ early RNA expression was reduced to approximately the level of wild type expression. Control co-transfections using the same amounts of control constructs E-RZ, a promoter-less version of αE-RZ and Py-CMV, the same as αE-RZ but lacking polyoma early antisense regions (FIG. 2A) showed no decrease in early RNA levels from 5'ssΔ (FIG. 4A, lanes 4 and 5). FIG. 4B shows the dose-response analysis. Increasing amounts of αE-RZ resulted in a striking diminution in 5'ssΔ early-strand RNA levels. DNA replication assays were performed to ensure that observations did not result from change in level of DNA replication.

To further illustrate the generality of the method, a vector using the Rous sarcoma virus promoter was used to drive expression of antisense RNA to the bacterial chloramphenicol acetyltransferase (CAT) gene in cotransfection experiments in mouse 3T3 cells. The assay shows that a six-fold excess of antisense-expressing plasmid leads to about a ten-fold reduction in CAT gene expression.

In another embodiment, specific sequences are incorporated into the nuclear antisense RNAs of the construct to increase their levels. Specifically, it is believed that a sequence containing part of a recognized RNA splicing signal will improve the stability of the nuclear RNA molecules when placed near their 5' ends.

In an alternate embodiment, the cis-ribozyme of construct αE-RZ is replaced with another ribozyme that is derived from the human hepatitis delta virus. It is reported that this ribozyme is far more efficient in vivo, compared to the ribozyme exemplified herein, and this may lead to higher levels of expressed nuclear antisense RNA.

Another embodiment of this invention incorporates sequences derived from the human Epstein Barr virus which will allow DNA replication. These sequences include the "oriP" sequence and the EBNA-1 gene; thus the vector will be able to replicate every time the cell replicates, and thereby be maintained in the cell over long periods of time.

In an alternate embodiment, the vector can be used to deliver not only antisense RNA but also antisense ribozymes that are capable of cleaving targeted RNA molecules in trans. There is growing literature on trans- ribozyme RNA cleavage, but again all systems use molecules that are targeted to the cytoplasm rather than the nucleus. (Steinecke, et al., *EMBO J.* 11:1525–1530 (1992)).

In another embodiment, the early region of the monkey virus SV40 (which infects all primate cells) can be removed and replaced with the nuclear antisense expression cassette as described above. The SV40 late region can be left intact, and these molecules will be introduced into monkey cells that express the SV40 early proteins (COS cells), thereby allowing efficient replication of these molecules. The result of this transfection will be the production of non-viable progeny virus particles, which are capable of expressing antisense RNA. Virus can be recovered from transfected cultures of COS cells and used to infect progeny cells. These viruses can enter cells and express the antisense genes, but are incapable of replication and cannot express SV40 late-region genes. This will allow delivery of nuclear antisense molecules efficiently and simultaneously to a large number of cells, including human cells.

This invention can be formulated in a preparation comprising the construct and a physiologically acceptable carrier. The preparation of this invention can be administered orally (e.g., capsular, tablet or liquid formulation), parenterally (e.g., intramuscularly, intravenously, subcutaneously) or topically in dosage formulations containing physiologically acceptable vehicle and optional adjuvants and preservatives. Suitable physiologically acceptable vehicles include saline, sterile water, Ringer's solution and isotonic sodium chloride solutions. The specific dosage level of active ingredient will depend upon a number of factors, including biological activity of the particular preparation, age, body weight, sex, general health and clinical diagnosis.

This invention also has utility as a research tool, in that it allows the regulation and inhibition of expression of various genes. This ability to selectively inhibit gene expression has potential for the study of virtually any gene expressed in eukaryotic cells.

The following Examples are offered for the purpose of illustrating the present invention and are not to be construed to limit the scope of this invention.

Exemplification

The teachings of all references are incorporated herein by reference.

EXAMPLE 1

Materials

All restriction enzymes, T4 DNA ligase, large fragment of DNA polymerase (Klenow enzyme) and T4 polynucleotide kinase were from New England Biolabs and were used as suggested by the manufacturer. Calf intestine alkaline phosphatase was from Boehringer Mannheim. An RNAse T1/T2 mixture was made and used as described (Lichtler et al., *Biotechniques* 12:231–232 (1990)). T3 and T7 RNA polymerases and RNAse free RQ1 DNAse were from Promega Corp. The Random Primers DNA Labeling System was from Bethesda Research Laboratories. [α-$^{32}$P]UTP and [α-$^{32}$P]dATP were from Amersham Corp. GeneScreen Plus hybridization transfer membranes were from NEN Products of Dupont and used as recommended. Oligonucleotides were synthesized using a Milligen/Biosearch cyclone DNA synthesizer and phosphoramidite chemistry.

EXAMPLE 2

Plasmid Constructions

Standard DNA cloning techniques (Maniatis et al., *Cold Spring Harbor Laboratory Manual,* Cold Spring Harbor Laboratory, Cold Spring Harbor, N.Y., 1982) were used in the construction of all plasmids. Polyoma virus strain 59RA (Feunteun et al., *Proc. Natl. Acad. Sci. USA* 68:283–288 (1986)) was cloned into the EcoRI site of a modified pUC18 vector and was used as the wild type virus. Constructs 5'ssΔ and ALM were described previously (Adami and Carmichael, Ibid., Barrett et al., Ibid.). Plasmid BS-RZ was generated by inserting annealed oligonucleotides comprising the histone stem loop-ribozyme oligonucleotide shown in FIG. 2B into pBlueScript SKII opened with EcoRV and SmaI. To create E-RZ, nt 359–2908 of 59RA (using the numbering system of Soeda et al., Nature 283:445–453 (1980)) were inserted at the BamHI site of BS-RZ that had been filled in with Klenow enzyme. The CMV promoter excised from pcDNA I/Amp (Invitrogen Corp.) with EcoRV (nt 3023) and DraI (nt 2276) was inserted at the filled-in BamHI site of polyoma strain 59RA to create Py-CMV. Construct αE-RZ was created by inserting the Klenow-filled NarI-HindIII fragment of Py-CMV containing the polyoma replication origin and the CMV promoter into the SmaI site of E-RZ. Construct Ribo-Ava was created by inserting the AvaI fragment spanning the cleavage site of the ribozyme of αE-RZ. The clones used to generate RNA probes Ea and L4 were described previously (Liu and Carmichael, Ibid.).

EXAMPLE 3
Cell Culture, Transfection, Infection and RNA Isolation

Mouse NIH 3T3 and 3T6 cells were maintained and propagated as described by Cahill et al. (*J. Virol.* 64:992–1001 (1990)). Cells were seeded at a density of 1× $10^6$/150-mm plate 24 hours prior to transfections or infection. For transfection, the polyoma virus constructs (wild type, ALM and 5'ssΔ) were released from the recombinant plasmids with proper restriction enzymes (EcoRI or BamHI) and recircularized with T4 DNA ligase under diluted conditions (<10 µg DNA/ml). Transfection followed a standard BES procedure (Chen and Okayama, *Mol. Cell. Biol.* 7:2745–2752 (1987)). Construct αE-RZ was co-transfected into NIH 3T3 cells along with mutant 5'ssΔ at various molar ratios as indicated in FIGS. 3 and 4. Infection of NIH 3T6 cells with strain 59RA was as described by Adami and Carmichael (*Nucleic Acids Res.* 15:2593–2610 (1987)). A single step method using guanidinium thiocyanate (Xie and Rothblum, *BioTechniques* 11:325–327 (1991)) was used to isolate total RNA. In brief, cells were lysed with a solution containing 4M guanidinium thiocyanate, 25 mM sodium citrate pH 7.0, 0.5% Sarcosyl and 0.1 M mercaptoethanol. The lysate was combined with an equal volume of water-saturated phenol and one fifth volume of chloroform and then allowed to sit on ice for 15 minutes. After centrifugation the aqueous phase was removed and precipitated with an equal volume of isopropanol. Nuclear and cytoplasmic RNAs were isolated as described by Hyde-DeRuyscher and Carmichael (*J. Virol.* 64:5823–5832 (1990)). Nuclear and cytoplasmic RNA samples isolated 48 hours post transfection were analyzed by an RNAse protection assay with the RNA probe Ribo-Ava (see FIG. 2A). To minimize DNA contamination, the RNA samples were extracted twice with acidic phenol as described in Liu and Carmichael, Ibid.

EXAMPLE 4
RNAse Protection Assays

The clones used to generate RNA probes were linearized with appropriate restriction enzymes. Following in vitro transcription using T3 or T7 RNA polymerase and [α-$^{32}$p] UTP, DNA templates were removed by RQ1 DNAse digestion in combination with acid-phenol extraction. The lengths of protected probes were 421 nt for unprocessed antisense transcripts containing cis-ribozyme, 337 nt for transcripts cleaved by the cis-ribozyme, and 305 nt for early antisense transcripts deriving from mutant 5'ssΔ. The labeled RNA probes were hybridized in excess to RNA samples at 57–60° C. overnight (Adami et al., *J. Virol.* 63:85–93 (1989)). The resulting hybrids were then digested with T1/T2 mixture (Lichtler et al., Ibid.) at 37° C. for 2 hours. The reactions were stopped by adding 0.8 volumes of GTCN solution described above containing 20 µg glycogen as carrier. Undigested RNA fragments were then precipitated with an equal volume of isopropanol at −70° C. Samples recovered by centrifugation were resolved on 6% denaturing polyacrylamide sequencing gels. Quantitation of band intensities was performed using a Betagen Betascope Blot Analyzer. Control experiments using variable amounts of RNA probes confirmed that all RNAse protection experiments were carried out in probe excess.

EXAMPLE 5
DNA Replication Assays

Episomal DNA was isolated as described by Hirt (*J. Mol. Biol.* 26:365–369 (1967)) and digested with an excess of DpnI, EcoRI and BamHI. Southern blot analysis of DNA replication was as described (Cahill et al., Ibid.) with a probe made by random priming the AvaI fragments (nt 657–1016) of 59RA.

Equivalents

Those skilled in the art will recognize, or be able to ascertain, using no more than routine experimentation, many equivalents to the specific embodiments of the invention described herein. Such equivalents are intended to be encompassed by the following claims:

What is claimed is:

1. A DNA construct comprising:
   a. a transcriptional promoter;
   b. a DNA segment encoding a trans-ribozyme; and
   c. a sequence encoding a cis-ribozyme;
   such that expression of the DNA segment produces a trans-ribozyme which cleaves a ribonucleotide sequence transcribed from a gene, and said trans-ribozyme expressed from the DNA segment is accumulated in the cell nucleus and inhibits the expression of said gene.

2. The construct of claim 1 wherein the transcriptional promoter segment is an inducible promoter.

3. An isolated cell containing the construct of claim 1.

4. A vector having incorporated therein the construct of claim 1.

5. The vector according to claim 4 wherein said vector is a plasmid.

6. A composition comprising the construct of claim 1 and a physiologically acceptable vehicle.

7. A composition comprising the vector of claim 4 and a physiologically acceptable vehicle.

8. A composition comprising the vector of claim 5 and a physiologically acceptable vehicle.

9. An isolated cell containing the vector of claim 4.

10. A method of inhibiting the expression of a gene in a cell comprising introducing the construct of claim 1 into said cell.

11. A method of inhibiting the expression of a gene in a cell comprising the steps of:
    a. introducing the construct of claim 1 into said cell whereby a transformed cell is obtained; and
    b. expressing the RNA segment to thereby inhibit the expression of said gene.

12. A DNA construct comprising:
    a. a human cytomegalovirus promoter of Rous sarcoma virus promoter,
    b. a DNA segment encoding a trans-ribozyme; and
    c. a sequence encoding a cis-ribozyme;
    such that expression of the DNA segment produces a trans-ribozyme which cleaves ribonucleotide sequence transcribed from a gene, and said trans-ribozyme expressed from the DNA segment is accumulated in the cell nucleus and inhibits the expression of said gene.

13. An isolated cell containing the construct of claim 12.

14. A vector having incorporated therein the construct of claim 12.

15. The vector according to claim 14 wherein said vector is a plasmid.

16. A composition comprising the construct of claim 12 and a physiologically acceptable vehicle.

17. A composition comprising the vector of claim 14 and a physiologically acceptable vehicle.

18. A composition comprising the vector of claim 15 and a physiologically acceptable vehicle.

19. A method of inhibiting the expression of a gene in a cell comprising introducing the construct of claim 12 into said cell.

20. A method of inhibiting the expression of a gene in a cell comprising the steps of:
    a. introducing the construct of claim 12 into said cell whereby a transformed cell is obtained; and
    b. expressing said RNA segment to thereby inhibit expression of said gene.

* * * * *